United States Patent [19]

Krespan et al.

[11] Patent Number: 5,026,801

[45] Date of Patent: Jun. 25, 1991

[54] POLYHALODIHYDRODIOXINS AND POLYHALODIOXOLES

[75] Inventors: Carl G. Krespan; Paul R. Resnick, both of Wilmington, Del.

[73] Assignee: E. I. Du Pont de Nemours and Company, Wilmington, Del.

[21] Appl. No.: 408,593

[22] Filed: Sep. 18, 1989

[51] Int. Cl.$^5$ .................... C08F 116/00; C07D 319/14
[52] U.S. Cl. ..................... 526/247; 549/362; 549/380
[58] Field of Search ................. 526/247; 549/380, 362

[56] References Cited

U.S. PATENT DOCUMENTS

| | | | |
|---|---|---|---|
| 2,925,424 | 2/1960 | Simmons | 260/340.7 |
| 3,308,107 | 3/1967 | Selman et al. | 260/87.5 |
| 3,316,216 | 4/1967 | Fawcett et al. | 260/63 |
| 3,324,144 | 6/1967 | Coe et al. | 260/340.9 |
| 3,532,725 | 10/1970 | Dorfman et al. | 260/404 |
| 3,555,100 | 1/1971 | Garth et al. | 260/615 |
| 3,557,165 | 1/1971 | Dorfman et al. | 260/404 |
| 3,749,791 | 7/1973 | Terrell et al. | 424/278 |
| 3,865,845 | 2/1975 | Resnick | 260/340.9 |
| 3,978,030 | 8/1976 | Resnick | 526/247 |
| 4,343,742 | 8/1982 | Muffler et al. | 549/380 |
| 4,429,143 | 1/1984 | Anderson et al. | 549/450 |
| 4,431,786 | 2/1984 | Squire | 526/247 |
| 4,485,250 | 11/1984 | Squire | 549/455 |
| 4,496,750 | 1/1985 | Anderson et al. | 549/455 |

OTHER PUBLICATIONS

Coe et al., J. Fluor. Chem. 1975, 6, 115–128.
Schwertfeger et al., Angew. Chem. Int. Ed. Engl. 1980, 19, 126.
Luedicke et al., Naturwiss 1953, 40, 363.

*Primary Examiner*—Joseph L. Schofer
*Assistant Examiner*—Mark Nagumo

[57] ABSTRACT

This invention is directed to halodihydrodioxins, their preparation and their polymers, which provide amorphous homopolymers that are resistant to ring opening side reactions. The resulting polymers can be used for films and thermally stable molded objects, coatings for substrates such as wood, glass, paper and metal and for protective packaging. This invention also concerns the preparation of polyhalogenated dioxoles.

23 Claims, No Drawings

POLYHALODIHYDRODIOXINS AND POLYHALODIOXOLES

BACKGROUND OF THE INVENTION

1. Field of the Invention

This invention is directed to halodihydrodioxins, their preparation and their polymers. The monomers of this invention provide amorphous homopolymers and copolymers that are resistant to ring opening side reactions during polymerization. The resulting polymers which are stable can be used for films and thermally stable molded objects, coatings with selected characteristics for substrates such as wood, glass, paper and metal and for protective packaging. This invention also concerns the preparation of polyhalogenated dioxoles.

2. Discussion of the Prior Art

P. L. Coe; P. Dodman; J. C. Tatlow; J. Fluor. Chem. 1975, 6, 115–128, describe the preparation of hexafluoro-p-dioxene in 18% yield by the dehydrofluorination of 2H-heptafluoro-p-dioxane under drastic conditions (fused potassium hydroxide at 150 degrees to 160 degrees). The authors also comment on the difficulty of dehydrofluorination of the —O—CFH—CF$_2$ in some situations.

W. Schwertfeger; G. Siegemund; Angew. Chem. Int. Ed. Engl. 1980, 19, 126 disclose the preparation of fluorinated 1,4-dioxanes by the reaction of perfluorinated vicinal dicarbonyl compounds with ethylene dimesylate and potassium or cesium fluoride.

U.S. Pat. No. 4,343,742, by Muffler et al. claims a process for the manufacture of 2,3-perfluoro 1,4 dioxane.

U.S. Pat. No. 2,925,424 discloses cyclic fluoroketals of the formula:

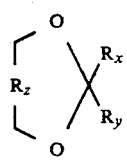

prepared by reacting fluoroketones with β-haloethanol. R$_x$ and R$_y$ are perhalohydrocarbyl radicals of from 1 to 7 carbon atoms and R$_z$ is a divergent hydrocarbyl or halohydrocarbyl radical of 1 to 12 carbon atoms.

U.S. Pat. Nos. 3,865,845 and 3,978,030 disclose fluorinated dioxoles of the formula:

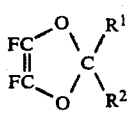

where R$^1$ and R$^2$ are both perhalogenated hydrocarbyl radicals of 1 to 3 carbon atoms containing at least one F atom, and preparation of said dioxoles by reacting the corresponding dioxolanes with Mg. The dioxolanes are prepared by the fluorination with SbF$_3$-SbCl$_5$ at 120° C. of 2,2-bis-(perhaloalkyl)-4,4,5,5,-tetrachloro-1,3-dioxolanes, which in turn are prepared by chlorination of the dioxolanes described in U.S. Pat. No. 2,925,424 cited above.

U.S. Pat. No. 3,555,100 discloses the decarbonylation of fluorocarboxylic acid fluorides in the presence of SbF$_5$.

U.S. Pat. No. 3,308,107 discloses perfluoro-2-methylene-4-methyl-1,3-dioxolane, its preparation from perfluoro-2,4-dimethyl-2-fluoroformyl-1,3-dioxolane and polymers thereof.

U.S. Pat. No. 3,532,725 discloses the photochlorination of alkyl and aralkyl ester groups of fluorinated esters in the presence of Cl$_2$, UV radiation and optionally, CCl$_4$ as solvent.

U.S. Pat. No. 3,557,165 discloses the conversion to acyl halides, in the presence of Lewis acids, of fluorinated esters wherein the ester groups contain polyhalogenated alkyl or aralkyl groups. The disclosed Lewis acids include FeCl$_3$, SbCl$_5$, ZnCl$_2$, BF$_3$, BCl$_3$, MoCl$_5$, tin chlorides and other metal chlorides, bromides and iodides.

U.S. Pat. No. 3,316,216 discloses the preparation of fluorinated dioxolanes of the formula:

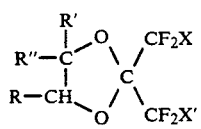

where R, R' and R" can include H, hydrocarbyl, haloalkyl and various other carbon-containing groups, and X and X' can include H, halogen and perfluoroalkyl, from fluoroketones and epoxides U.S. Pat. No. 3,324,144 discloses fluorodioxolanes of the formula:

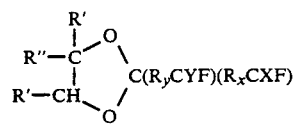

prepared from ketones and epoxides.

U.S. Pat. No. 3,749,791 discloses halogen-substituted 2,2-bis(trifluoromethyl)-1,3-dioxolanes of the formula:

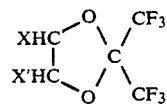

where X is Cl or F and X' is H, Cl, or F, and their preparation is by halogenation of 2,2-bis(trifluoromethyl)-1,3-dioxolane.

U.S. Pat. No. 4,496,750 and U.S. Pat. No. 4,429,143 disclose the composition and a process for the preparation of halogenated dioxolanes of the formula:

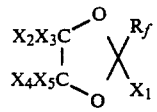

wherein:

X$_1$ is selected from the group consisting of Cl, F, COF, COCl, CO$_2$CCl$_3$, CO$_2$R and CO$_2$M;

R is selected from the group consisting of H and alkyl of 1 to 4 carbon atoms;

R$_F$ perfluoroalkyl of 1 to 4 carbon atoms;

M is selected from the group consisting of alkali metal ion and ammonium;

$X_2$, $X_3$, $X_4$ and $X_5$, independently, are selected from the group, consisting of H, Cl and F; with the proviso that when $X_2$, $X_3$, $X_4$ and $X_5$ are each H, $X_1$ is $CO_2R$ or $CO_2M$.

M Luedicke; W. Stumpf, *Naturwiss* 1953, 40, 363 describe the synthesis of heptachlorodioxane by chlorination of dioxane.

SUMMARY OF THE INVENTION

The invention concerns novel monomers, polymers and copolymers of dihydrodioxins of the general structure:

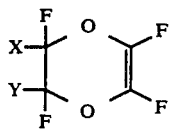   I wherein:
X and Y independently are F or $R_F$ but are not both F;
$R_F$ is a $C_1$ to $C_8$ linear or branched perfluoroalkyl with or without in-chain oxygen;
X and Y together can be a perfluoroalkylene chain equal to $(CF_2)_n$, where $n = 2-4$.

The invention also concerns polymers and copolymers of

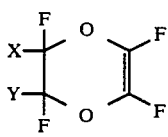

where X and Y are both F.

This invention also concerns dehalogenation processes for making monomer I, perfluoro-2,3-dihydro-1,4-dioxin and halogenated dioxoles.

Hereafter, the term polymer(s) is intended to include homopolymers and copolymers.

The invention also concerns coatings and films of polymers described herein.

DETAILS OF THE INVENTION

The invention concerns novel polymers and copolymers produced from monomers of the formula:

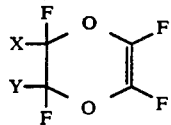   I where X and Y are independently F or $R_F$ and $R_F$ can be $C_1$ to $C_8$ linear or branched perfluoroalkyl, with in-chain ether optionally present. The invention also concerns novel monomers of the formula above in which X and Y are independently $R_F$ with the limitation that X and Y are not both F and with X and Y taken together equal to $(CF_2)n$, where $n = 2-4$. The heptachlorodioxane starting material for the synthesis of perfluoro-2,3-dihydro-1,4-dioxin, can be produced by the method of M. Luedicke and W. Stumpf in *Naturwiss* 1953, 40,363. The synthesis is described in Example 1, below. The resulting monomer can be homopolymerized or copolymerized with a perfluoropropionyl peroxide catalyst.

The process for producing Structure I where $X = Y = F$ proceeds as follows:

Heptachlorodioxane,

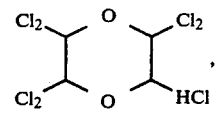

is synthesized by chlorination of dioxane. Perchloro2,3-dihydro-1,4-dioxin, shown below, is produced by the reaction of heptachlorodioxane with sodium hydroxide.

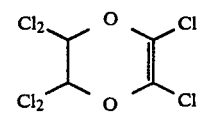

Fluorine containing species of dioxins are prepared by treating the chlorinated species above with various fluorinating agents, including, but not limited to, $SbF_3$ in the presence of $SbCl_5$ and HF in the presence of $SbCl_5$. When the above perchloro-2,3-dihydro-1,4-dioxin is treated with a fluorinating agent, a total of four fluorine atoms can be introduced to form:

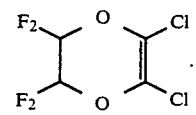

The fluorination process proceeds at 1-20 atmospheres ($10^5$ to $2 \times 10^6$ Pa) of pressure and 40° C.-150° C. The process generally takes 0.5 to 24 hours. The reactor for the fluorination with a $SbF_3$ fluorinating agent can be glass or Hastelloy. Hastelloy is used for HF reactions.

The 2,2,3,3-tetrafluoro-5,6-dichloro-2,3-dihydro-1,4-dioxin shown above is reacted with chlorine to form:

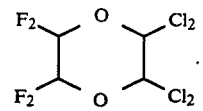

The chlorination process is carried out by ultraviolet irradiation of the mixture of reactants at 20°-80° C. until chlorine is no longer absorbed, generally within 0.5 hour after a slight excess of chlorine is introduced. Glassware is preferred for convenience, but metal reactors can also be used at 1-5 atmospheres of pressure An inert solvent such as $CCl_4$ or $ClCF_2CFCl_2$ is optional.

Fluorination is carried out as described above at 70°-150° C. to give a mixture of products of the formulas:

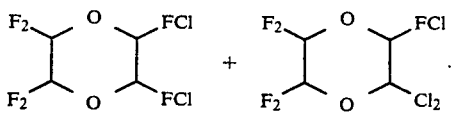

Treating the 2,3-dichloro-2,3,5,5,6,6-hexafluoro-1,4-dioxane and 2,2,3-trichloro-3,5,5,6,6-pentafluorodioxane shown above with zinc or magnesium under N₂ in the optional presence of a metal activating agent such as but not limited to, 1,2-dibromoethane or bromine yields the following products:

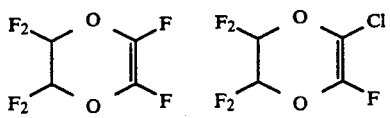

The dechlorination step is normally done at about 1 atm pressure ( $1.013 \times 10^5$ Pa) but can be done at higher pressure if necessary. The temperature for the reaction is 70° C.–140° C. The expected reaction time is 0.5–4.0 hours. Zinc is the preferred metal. Solvents for the process include but are not limited to polar aprotic materials such as DMF, benzonitrile, THF, diglyme, tetraglyme, acetonitrile, N-methyl pyrrolidone, 1,3-dimethyl-2-imidazolidinone, hexamethyl phosphoramide and N,N-dimethyl acetamide. Preferred solvents are DMF and N-N-dimethyl acetamide. The process is carried out in an inert atmosphere, preferably nitrogen.

Perfluoro-2,3-dihydro-1,4-dioxin is easily purified by fractional distillation.

Free radical initiated polymerization of the perfluoro-2,3-dihydro-1,4-dioxin gives a homopolymer of the formula:

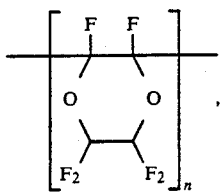

where n is an integer in excess of 5, typically 10 to 20, and where the molecular weight is at least 1000. (If n=10, MW=1940. Generally, polymers are greases until n approaches 1000.)

Useful free radical initiators include: perfluoropropionyl peroxide, benzoyl peroxide, t-butyl hydroperoxide and azobis(isobutyronitrile).

The various polyfluorinated dihydrodioxins can be copolymerized with a variety of olefins including but not limited to vinyl fluoride, vinylidene fluoride, trifluoroethylene, tetrafluoroethylene, chlorotrifluoroethylene, hexafluoropropylene, ethylene, perfluoro(methyl vinyl ether), vinyl acetate, perfluoro(ethyl vinyl ether), perfluoro(propyl vinyl ether) and perfluoro(butyl vinyl ether). Typically copolymers have a molecular weight of at least 10,000. Copolymerization goes more readily than homopolymerization. The copolymers can include 1% or more by weight of the polyfluorodihydrodioxin.

A preferred monomer of the generic formula:

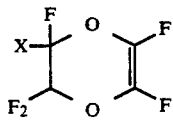

wherein X=CF₃ can be synthesized from the epoxide by means of the process illustrated in Example 2 according to the following reaction steps:

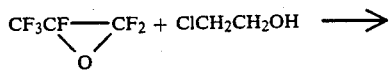

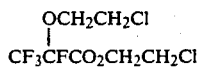

This reaction occurs at 1–20 atm pressure, within a temperature range of 25°–100° C. and over a period of 0.5–24 hours.

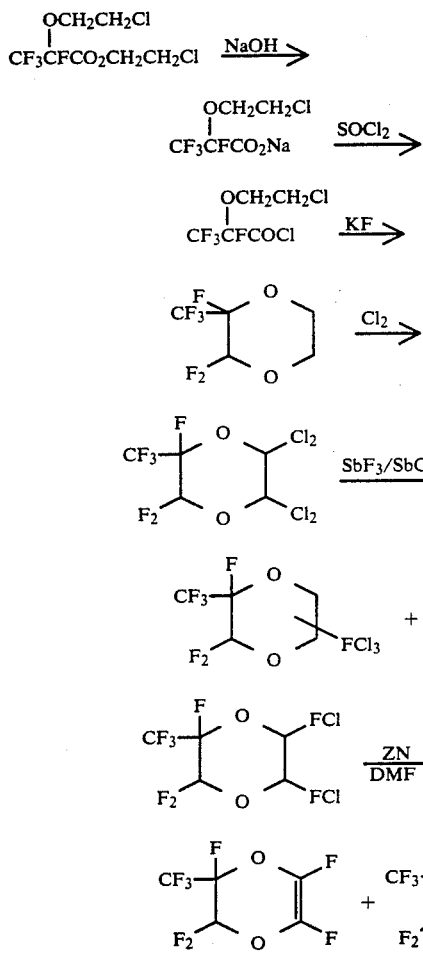

Monomer I where x=CF₃ and y=F can be homopolymerized under free radical catalysis as described in Example 2(g) to yield a polymer in the form

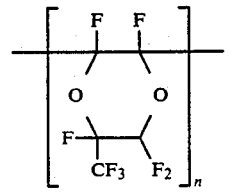

Copolymerization of monomer I where x=CF₃ and y=F using perfluoropropionyl peroxide catalyst with tetrafluoroethylene in the presence of CFCl₂CF₂Cl at a reaction temperature of about 20° C. produces a polymer of the form

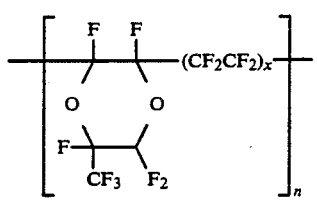

The resulting copolymer is stable and a film of said copolymer is clear and tough.

This invention also concerns a process for the effective dechlorination of a chlorinated dioxolane in the presence of zinc or magnesium, as described above for the dioxane, in the optional presence of a metal activating agent such as but not limited to 1,2-dibromoethane and bromine and in the presence of a solvent. Such solvents include DMF, N,N-dimethyl acetamide and N-methyl pyrrolidone. A typical reaction is shown below.

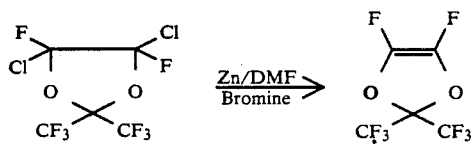

See Examples 8, 9 and 10.

This method is also advantageous for the preparation of chlorofluoro and dichlorodioxoles as it gives high yields and avoids hydrodioxole impurities.

The principles and practice of the present invention are illustrated below by Examples which are only exemplary thereof and it is not intended that the invention be limited thereto.

In the following Examples, parts and percentages are by weight and temperatures are in degrees Celsius.

EXAMPLE 1

Perfluoro-2,3-dihydro-1,4-dioxin and Its Homopolymer

The synthesis of heptachlorodioxane (1) by chlorination of dioxane is reported in Luedicke, M.; Stumpf, W., *Naturwiss* 1953, 40, 363.

30 a A solution of 60.1 g (0.183 mol) of crude 1 in 100 g of CCl₄ was cooled at 10°-20° C.; in an ice bath while a solution of 40.0 g (1.0 mol) of NaOH in 500 mL of methanol was added slowly. The mixture was stirred another 10 min. at 10°-20° C., then diluted with 2 L of water. The lower layer was washed with 500 mL of water, dried over CaSO₄, and filtered.

Fractionation afforded 39.4 g (74%) perchloro-2,3-dihydro-1,4-dioxin (2), bp 69°-71° C. (2.5 mm).

IR(CCl₄): 1670 cm$^{-1}$(C=C).

NMR (CDCl₃): 13C 124.6 (=CClO—) and 108.5 ppm (—CCl₂O—).

Anal. Calcd. for $C_4Cl_6O_2$: C, 16.41; Cl, 72.66;
Found:
C, 16.10; Cl, 72.96

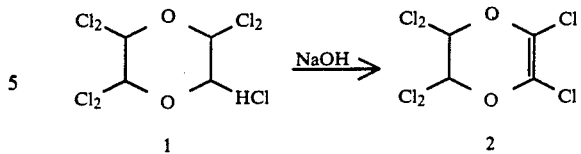

b. To a stirred suspension of 488 g (2.5 mol) of SbF₃ in 293 g (1.0 mol) of 2 was added 10 mL of SbCl₅. Following an exotherm to 45° C., the mixture was stirred at 50° C., for 1 hr, 60° C. for 2 hrs, then after addition of 5 mL of SbCl₅ at 80° C. for 1 hr. Another 5 mL of SbCl₅ was added and the mixture refluxed (98°-93° C.) for 1 hr, after which a final 5 mL of SbCl₅ was added and the mixture refluxed (93°-88° C.) for 1 hr. Volatile product was removed under vacuum, stirred with NaF, filtered and distilled to give 118.4 g (52%) of 2,2,3,3-tetrafluoro-5,6-dichloro-2,3-dihydro-1,4-dioxin (3), bp 44°-48° C. (200 mm).

IR (CCl₄): 1675 (C=C), 1250-1100 (CF, C-O), 800 cm$^{-1}$ (CCl).

NMR (CDCl₃): $19_F$ ϕ—92.8 (s, —CF₂O—).

GC/MS: m/e 226, 228, and 230 (M+) with expected fragmentation pattern.

Anal. Calcd. for $C_4Cl_2F_4O_2$:
Cl, 31.24;
Found: Cl, 30.87

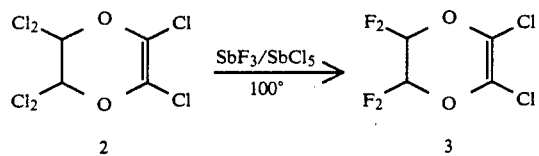

c. A solution of 118 g (0.52 mol) of 3 in 200 mL of CFCl₂CF₂Cl was stirred under a −80° condenser and irradiated with a sunlamp while chlorine was passed in until reaction ceased. Distillation gave 127.4 g (82%) of 2,2,3,3-tetrachloro-5,5,6,6-tetrafluoro-1,4-dioxane (4), bp 65° C. (40 mm).

IR (neat): 1250-1100 (CF, C-O), 760 cm$^{-1}$.

NMR (CDCl₃) $19_F$ ϕ—79.6 (s, —CF₂O—).

GC/MS: m/e 261, 263, 265, and 267 (M+-Cl), with expected fragmentation pattern.

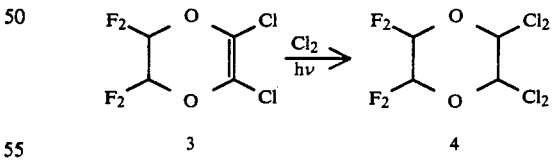

d. A stirred suspension of 143.2 g (0.40 mol) of SbF₃ in 117 g (0.39 mol) of 4 was treated with 5 mL of SbCl₅ and refluxed for 4 hr. An additional 3 mL of SbCl₅ was added, and the mixture was stirred at reflux for another 6 hr (final temp=83° C.). Volatiles were transferred under vacuum, treated with CaSO₄, filtered and distilled to afford 75.1 g (73%) of 2,3-dichloro-2,3,5,5,6,6-hexafluoro-1,4-dioxane (5), bp 79°-81° C. $19_F$ NMR spectrum indicated both isomers of 5 to be present. Further fractionation gave 11.8 g (11%) of 2,2,3-trichloro-3,4,4,5,5-pentafluoro-1,4-dioxane (6), bp 113° C. The 19F NMR spectrum fit the assigned structure.

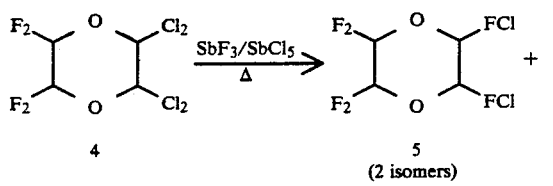

e. A suspension of 39.2 g (0.60 mol) of zinc dust in 300 mL of dry DMF was stirred under $N_2$ while 5 mL of 1,2-dibromoethane was added. Then a small portion of 74.0 g (0.28 mol) of dichloride 5 was added, and the mixture was stirred and heated. When an exothermic reaction started (about 75° C.), the rest of 5 was added dropwise at a rate sufficient to maintain 110°–120° C. in the pot while product was collected in a −80° C. trap. When the addition was completed, the mixture was heated to reflux to drive out the last of the product. Fractionation of the crude volatile product gave 24.5 g (45%) of pure perfluoro-2,3-dihydro-1,4-dioxin (7), bp 18°–19.5° C. IR (gas): 1845 cm$^{-1}$ (w, C=C).

The mass spectrum confirmed the assigned structure.

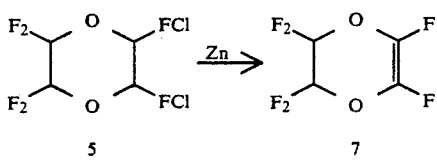

f. A mixture of 5.5 g (0.028 mol) of 7 and 0.2 mL of 0.8% perfluoropropionyl peroxide catalyst in $CFCl_2CF_2Cl$ was sealed in a 25 mL polymer tube and heated at 40° C. for three days. Then 0.1 mL of catalyst solution was added, and the tube was again thermostatted at 40° C. for one day. The addition was repeated and reaction continued another three days. Evaporation of volatiles at 0.1 mm gave 1.90 (35%) of clear, colorless solid polymer. The polymer was soluble in $CFCl_2CF_2Cl$ as well as in the monomer, as expected for an amorphous material. On the melting point block, softening and flow occurred at 110°–120° C. DSC gave $T_g=110°$ C. TGA showed the polymer to be stable to 350° C., then 11% wt loss to 440° C.

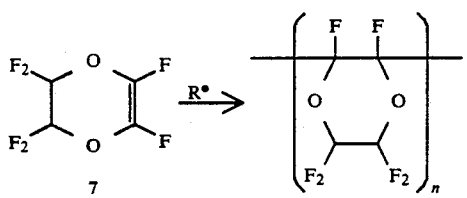

EXAMPLE 2

Perfluoro-5-methyl-2,3-dihydro-1,4-dioxin, Its Homopolymer, and Copolymer with TFE a. A 1-L Hastelloy-lined metal tube was charged with 480 g (6.0 mol) of 2-chloroethanol and 300 g (1.8 mol) of hexafluoropropene epoxide, then heated at 60° C. for 18 hrs. The liquid product was agitated with 2 L of ice water, washed with 400 mL of water, dried over $CaSO_4$, filtered and distilled to afford 351 g (68%) of ester 8, bp 74°–78° C. (1.1 mm).

IR (neat): 2970 and 2900 (satd CH), 1775 (C=O), 1250–1100 cm$^{-1}$ (CF, C—O).

NMR (CDCl$_3$): 1H δ 4.57 (t, $J_{HH}$5.5Hz, 2H, $CO_2CH_2$), 4.05 (t, $J_{HH}$5.5Hz, 2H, $OCH_2$), 3.73 (m, 4H, $CH_2Cl$); 19$_F$ φ−81.7 (d, $J_{FF}$3Hz, 3F, $CF_3$), −132.0 (q, $J_{FF}$3Hz, 1F, CF).

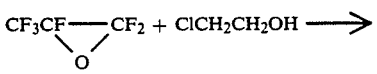

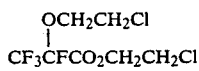

b. A solution of 40 g (1.0 mol) of sodium hydroxide in 200 mL of methanol was stirred at 40°–50° C. while 130 g (0.45 mol) of ester 8 was added dropwise. The mixture was stirred an additional 30 min, then evaporated to near dryness under vacuum. Thionyl chloride (179 g, 1.5 mol) was added cautiously, then 1 mL of dimethylformamide, and the mixture was stirred at 60°–80° C. until evolution of gas had nearly ceased (6 hrs). Addition of another 60 g (0.5 mol) of thionyl chloride and heating at 80° C. caused only slow evolution of gas. Volatiles were transferred under vacuum, then fractionated to give 90.1 g (82%) of 2-(2-chloroethoxy)-2,3,3,3-tetrafluoropropionyl chloride (9), bp 69°–70° C. (50 mm).

IR (CCl$_4$): 2960 and 2890 (satd. CH), 1800 (COCl), 1250–1100 cm$^{-1}$ (CF,C—O)

NMR (CDCl$_3$): 1H δ 4.08 (t, $J_{HH}$5Hz, 2H, $OCH_2$), 3.68 (t, $J_{HH}$5Hz, 2H, $CH_2Cl$); 19$_F$ φ −79.9 (d, $J_{FF}$3Hz, 3F, $CF_3$), −126.4 (q, $J_{FF}$3Hz, 1F, CF).

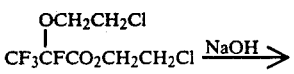

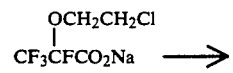

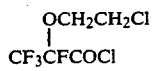

c. A mixture of 64.0 g (0.264 mol) of acid chloride 9, 58.1 g (1.0 mol) of dry KF, 150 mL of acetonitrile, and 150 mL of dry diglyme was stirred and heated at 85°–95° C. for 16 hrs. More KF (29.1 g, 0.50 mol) was added and heating was continued for 16 hrs. Another 29.1 g (0.50 mol) of KF was added and reaction continued at reflux (95° C.) until cyclization was complete (22 hrs). Distillation afforded a crude product fraction, bp 85°–155° C., which was washed with 2×200 mL of water to give 39.9 g (72%) of virtually pure 2,2,3-trifluoro-3-trifluoromethyl-1,4-dioxane (10). (Dioxane 10 has been reported previously from a similar ring closure of either 9 or the corresponding acid fluoride in U.S. Pat. No. 4,343,742. The synthesis of structure 9, however, is not that of our process.)

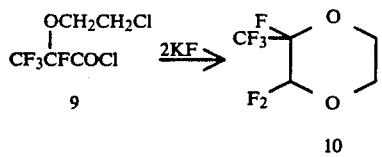

d. A solution of 50.0 g (0.24 mol) of dioxane 10 in 150 mL of CCl$_4$ was stirred under nitrogen at 25° C. while chlorine was added. No evidence of reaction was observed. Sunlamp irradiation caused an immediate exotherm and evolution of HCl through a −80° C. condenser. Reaction was continued with addition of chlorine as needed while the temperature was slowly raised to 80° C. over 17 hrs, at which point HCl evolution was very slow and GC indicated essentially one product. Fractionation gave 62.0 g (74%) of pure 2,2,3,3-tetrachloro-5-trifluoromethyl-5,6,6-trifluoro-1,4-dioxane (11), bp 63°–65° C. (30 mm).

IR (neat): 1300–1100 (CF,C—O), 800–700cm$^{-1}$ (CCl).

NMR (CDCl$_3$): 1H none; 19$_F\phi$ −73.8 (d of p, J$_{FF}$160, 17Hz, 1F A branch CF), −77.1 (d of d, J$_{FF}$160, 6Hz, 1F, B branch CF), −82.0 (d, J$_{FF}$17Hz, 3F, CF$_3$), −127.3 (d of d, J$_{FF}$17, 6Hz, 1F, CF).

Anal. Calcd. for C$_5$Cl$_4$F$_6$O$_2$:
Cl, 40.77; F, 32.77;
Found:
Cl, 41.08; F, 32.32

Side reactions such as ring cleavage are negligible, as shown by chlorination under sunlamp irradiation of 0.76 mol of neat 10 at 70°–95° C. over a 35-hr period to give 93% of pure 11, bp 64°–65° C. (30 mm).

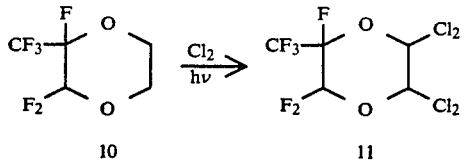

e. A mixture of 69.6 g (0.20 mol) of 11, 71.6 g (0.40 mol) of SbF$_3$, and 2 mL of SbCl$_5$ was stirred and heated slowly to 136° C. Heating was continued for 20 hrs with two more additions of SbCl$_5$ while the reflux temperature fell to 107.5° C. Products were transferred under vacuum and fractionated to afford 33.9 g (54%) of dichloro derivative 2,3-dichloro-5trifluoromethyl-2,3,5,6,6-pentafluoro-1,4-dioxane (13), bp 95°–100° C., as a mixture of isomers. NMR (CDCl$_3$): 19$_F \phi$ −66 to −84.5 (sev. m, OCFCl+OCF$_2$+CF$_3$), −127.5 to −133.2 (m, 1F, OCF (at least 3 of the 4 possible isomers)).

Anal. Calcd. for C$_5$Cl$_2$F$_8$O$_2$:
C., 19.07; Cl, 22.51; F, 48.26
Found: C, 18.98; Cl, 22.77; F, 47.90

Further distillation gave 21.0 g (32%) of trichloro isomers 12, bp 78°–80° C. (150 mm). NMR (CDCl$_3$):

19$_F\phi$ −69 to −83 (sev. m, 6F, OCFCl +OCF$_2$+CF$_3$), −127.2 to −132.2 (m, 1F, OCF (appears to be three isomers)).

Anal. Calcd. for C$_5$Cl$_3$F$_7$O$_2$:
C, 18.12; Cl, 32.09; F, 40.13
Found:
C, 18.14; Cl, 32.23; F, 40.07

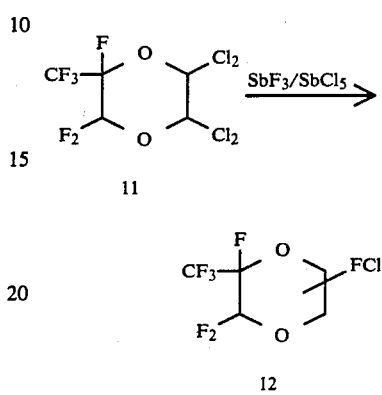

f. A mixture of 29.8 g (0.095 mol) of dioxane 13, 150 mL of dry DMF, 13.1 g (0.20 mol) of zinc dust, and 1 mL of 1,2-dibromoethane was stirred and heated under N$_2$ until the temperature reached 95° C., where obvious reaction occurred. The mixture was kept at 90°–95° C. for 2 hrs, during which time 15 g of distillate, bp 30°–45° C., was collected. GC/MS indicated a 57% yield of 14 and a 2% yield of 15 to be present. The crude product was washed with water, dried over CaSO$_4$, filtered, and distilled to give 7.1 g (31%) of perfluoro-2-methyl-2,3-dihydro-1,4-dioxin (14), bp 43° C.

IR (vapor): 1845 (C=C), 1300–1100 cm$^{-1}$ (CF, C—O).

NMR (CDCl$_3$): 19$_F\phi$ −80.3 (t of d, J$_{FF}$9, 3.0Hz, 3F, CF$_3$), −82.5 (d of d of q, J$_{FF}$149.2, 14.7, 10.3Hz, 1F, A branch of CFF), −92.9 (d of m, J$_{FF}$149.2Hz, 1F, B branch of CFF), −133.8 (t, J$_{FF}$15Hz, 1F, CF), −140.7 (d of d, J$_{FF}$47.8, 4.3Hz, 1F, A branch=CF), −144.2 (d, J$_{FF}$47.8Hz, 1F, B branch=CF).

MS: m/e 244 (M+), 197 (M+—COF), 169 (M+—CO—COF), 150 (CF$_3$CF=CF$_2$+), 131 (CF$_2$=CFCF$_2$+), 100 (C$_2$F$_4$+), 97 (CF$_3$CO+), 81 (C$_2$F$_3$+), 69 (CF$_3$+), 62 (FC=CF+), 50 (CF$_2$+), 47 (COF+).

A similar reaction on a 0.81 mol scale carried out at 100°–110° C. gave 103.9 g (53%) of 14, bp 42°–45° C., and 3.1 g (1.5%) of 15, bp 68°–71° C. Isomeric mixture 15 is best obtained as described in Example 3(a).

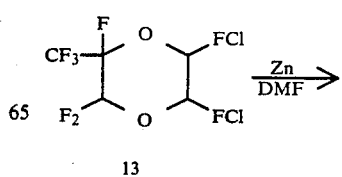

-continued

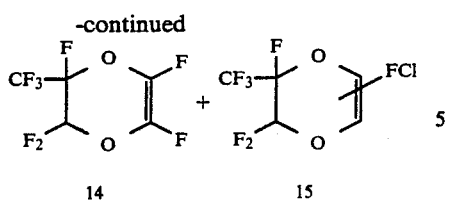

g. A sealed vial containing 1.3 g (5.3 mmol) of 14 and 8 drops of 3% perfluoropropionyl peroxide catalyst in CFCl$_2$CF$_2$Cl was heated at 40° C. for 1 day. Addition of catalysts was repeated and reaction run at 40° C. for 6 hrs, then addition of catalyst and reaction at 40° C. for 1 day was repeated. Finally, another 8 drops of catalyst was followed by reaction at 45° C. for 6 hrs. Viscosity of the mixture steadily increased during these operations. A sample of the solution placed on a glass plate and evaporated gave a clear film. The solution of polymer was evaporated to dryness and heated at 140° C. (0.1 mm) for 3 hrs to give a constant weight of 0.36 g (28%) of solid, amorphous homopolymer. On the melting point block, the glassy solid softened and flowed at 150°–160° C. Analysis by DSC indicated a broad Tg peaking at 51° C.; no other phase change was evident to over 300° C. TGA indicated major decomposition commencing at 360° C. until at 440° C. it reached 33%. Ring-opening is known to occur during polymerization of fluorodioxoles, even at modest temperature. No noticeable ring-opening of 14 occurred during polymerization, since no significant IR absorption near 1800 cm$^{-1}$ was detected for the strongly absorbing carbonyl group which would be introduced into the polymer by such ring-opening.

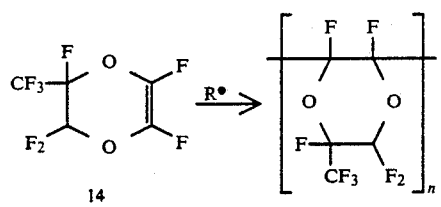

h. A 240 mL s.s-lined tube was charged with 5.0 g (21 mmol) of monomer 14, 50 mL of CFCl$_2$CF$_2$Cl, 5 mL of cold 3% perfluoropropionyl peroxide catalyst in CFCl$_2$CF$_2$Cl, and 30 g (0.30 mol) of tetrafluoroethylene. The tube was agitated as the mixture warmed; at 20° C., a rapid exotherm carried to 55° C. while the pressure fell to 0 psig. The solid, white polymeric product was heated under vacuum to constant weight, 29.2 g. Analysis of the volatiles by GC indicated the presence of about 1.5 g (30%) of recovered monomer 14. For the polymer, DSC on reheat showed a broad mp, Tonset 271° C, Tpeak 297° C. TGA: 2% weight loss to 400° C., 3.5% weight loss to 440° C. Thus, copolymerization of 14 with TFE occurs readily to give very stable copolymer. A film pressed at 330° C. and 1800 psi for 2 min was clear and tough.

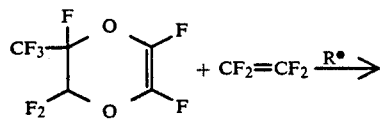

-continued

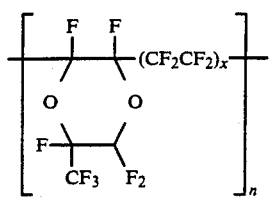

EXAMPLE 3

5-Chloro-2-trifluoromethyl-2,3,3,6-tetrafluoro-2,3-dihydrodioxin/6-Chloro-2-trifluoromethyl-2,3,3,5-tetrafluoro-2,3-dihydrodioxin Mixture (12) and Its Copolymer with Tetrafluoroethylene a. A suspension of 26.2 g (0.40 mol) of zinc dust in 250 mL of dry DMF was stirred under nitrogen and heated to 90° C. while a part of 69.8 g (0.21 mol) of 12 was added. The mixture was stirred at 90°–95° C. until reaction commenced after a brief induction period. The remainder of the dioxane was added at a rate sufficient to maintain 90°–95° C. in the pot while product was taken off at 30°–50° C. (150 mm). The addition required 45 min, after which 90° C. was maintained in the pot for 15 min. Pressure was slowly reduced to 20 mm while the reaction mixture cooled to transfer volatiles to a −80° C. trap. The crude product, 35.2 g, was fractionated to give 31.6 g (45%) of 15 as a mixture of isomers, bp 71°–73° C., contaminated with a small amount of DMF. A simple water wash removed the DMF, and a dried sample was analyzed.

IR (CCl$_4$): 1770 (C=C), 1250–1100 cm$^{-1}$ (CF, C—O). 1H NMR showed no proton present; 19$_F$ϕ MR indicated a 75:25 mixture of isomers. For the major isomer, NMR (CDCl$_3$): 19$_F$ϕ−80.0 (t of d, J$_{FF}$9.1, 3.1 Hz, 3F, CF$_3$), −81.2 (d of d of q, J$_{FF}$148.3, 14.5, 10.1 Hz, 1F, A branch CFF), −91.4 (d of m, J$_{FF}$148.3Hz, 1F, B branch CFF), −123.6 (d, J$_{FF}$4.9Hz, 1F, =CF), −134.3 (t of q, J$_{FF}$15.3, 3.3Hz, 1F, CF). For the minor isomer, 19$_F$ ϕ−80.4 (t of d, J$_{FF}$9.2, 3.1 Hz, 3F, CF$_3$), −83.2 (d of m, J$_{FF}$148Hz, 1F, A branch CFF), −93.7 (d of sextets, J$_{FF}$148, 7.9Hz, 1F, B branch CFF), −127.4 (s, 1F, =CF), −132.1 (t of m, J$_{FF}$15Hz, 1F, CF). MS: m/e 260/262 (M+), 213/215 (M+−COF), 150 (CF$_3$CF=CF$_2$+), 147 (M+−FC=CCl), 131 (CF$_2$=CFCF$_2$+), 100 (C$_2$F$_4$+), 97 (CF$_3$CO+), 85/87 (ClCF$_2$+), 81 (C$_2$F$_3$+), 78/80 (FC=CCl+), 69 (CF$_3$+), 66 (COF$_2$), 63/65 (COCl+), 50 (CF$_2$+), 47 (COF+).

Anal. Calcd. for C$_5$ClF$_{3l}$ O$_2$:
C, 23.05; Cl, 13.61;
Found:
C, 23.06; Cl, 13.52

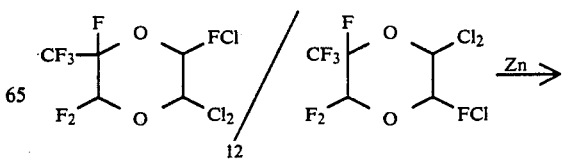

-continued $$\underset{15}{\overset{CF_3}{\underset{F_2}{\mid}}\overset{F}{\underset{O}{\subset}}=\overset{F}{\underset{Cl}{\subset}}} \Big/ \underset{}{\overset{CF_3}{\underset{F_2}{\mid}}\overset{F}{\underset{O}{\subset}}=\overset{Cl}{\underset{F}{\subset}}}$$

b. A 240 mL metal tube charged with 18.0 g (69 mmol) of pure 15, 50 Ml of CFCl$_2$CF$_2$Cl, 5 mL of cold 3% perfluoropropionyl peroxide catalyst in C$_F$Cl$_2$CF$_2$Cl, and 30 g (0.30 mol) of tetrafluoroethylene was agitated at 25° C. for 1 hr, then at 40° C. for 6 hrs. The pressure at 40° C. fell from 150 to 63 psi over 4 hrs. The polymeric product was dried by warming at 0.1 mm to constant weight, affording 20.3 g of white solid. GC indicated the volatiles contained 11.9 g (66%) of recovered 15. For the polymer, DSC showed twin melting points, Tonset 301° C., Tpeak 310, 314° C. TGA: 2% weight loss to 400° C., 16% weight loss to 445° C.

Anal. Calcd. for 58.5/1 copolymer:
Cl, 0.58;
Found:
Cl, 0.59, 0.57

$$15 + CF_2=CF_2 \xrightarrow{R\bullet} copolymer$$

EXAMPLE 4

Perfluoro-2,3-dimethyl-2,3-dihydro-1,4-dioxin, Its Homopolymer and Copolymer with Tetrafluoroethylene a. A mixture of 186 g (3.0 mol) of ethylene glycol and 250 mL of tetrahydrofuran was stirred under N$_2$ while 28.8 g (0.6 mol) of 50% NaH/mineral oil was added portionwise with cooling to maintain <40° C. When gas evolution had ceased, the mixture was stirred vigorously while 44 g (0.20 mol) of perfluorobutene-2 epoxide was distilled in over 2.5 hr and the temperature was maintained at 15°-25° C. The mixture was stirred an additional hour, then added to a solution of 60 mL of conc. H$_2$SO$_4$ in 1200 mL of water. The lower layer was separated, the aqueous layer was extracted with 200 mL of ether, and the combined organic layers were evaporated at 35° C. (15 mm) to 74 6 g viscous residue. 19F NMR and GC analysis indicated essentially one product, 16, to be present in addition to solvents.

The residue was treated with 65 g (0.5 mol) of thionyl chloride and 1 mL of DMF, then stirred at 60°-70° C. for 2.5 hr, then at 75° C. for 3.5 hr. Another 24.6 g (0.20 mol) of thionyl chloride and 1 mL of DMF were added, and reaction was continued at 75°-80° C. for 2.5 hr. Fractionation afforded 49.5 g (ca. 90%) of 3-(2-chloroethoxy)-1,1,1,3,4,4,4-heptafluorobutanone-2 (17) in 97.6% purity, bp 45° C. (70 mm) −58° C. (65 mm).

IR (CCl$_4$): 2964, 2895 (sat'd CH), 1793 and 1783 (C=O), 1250-1100 cm$^{-1}$ (CF, CO). The 1H and 19$_F$ NMR spectra, as well as the mass spectrum, fit the assigned structure.

$$CF_3CF\overset{O}{\underset{}{\diagdown\diagup}}CFCF_3 + NaOCH_2CH_2OH \longrightarrow adduct \xrightarrow{H_2O}$$

-continued $$\underset{}{\overset{OCH_2CH_2OH}{\underset{}{\mid}}}$$
$$CF_3CFC(OH)_2CF_3$$
$$\underset{\searrow}{SOCl_2} \quad 16$$
$$\underset{}{\overset{OCH_2CH_2Cl}{\underset{}{\mid}}}$$
$$CF_3CFCOCF_3$$

17 b. A mixture of 48 g (0.174 mol) of 17, 100 mL of dry acetonitrile, and 20.3 g (0.35 mol) of dry KF was refluxed under N$_2$ for 20 hrs. The mixture was poured into 500 mL of water, and the lower layer was removed. The aqueous layer was extracted with 150 mL of ether, and the combined organic layers were washed with water, dried over CaSO$_4$, filtered and distilled to give 40.2 g (89%) of 2,3-bis(trifluoromethyl)-2,3-difluoro-1,4-dioxane (18), bp 80°-84° C. (100 mm), as a mixture of two isomers.

$$\underset{}{\overset{OCH_2CH_2Cl}{\underset{}{\mid}}} + KF \longrightarrow \underset{F}{\overset{CF_3}{\underset{CF_3}{\mid}}}\overset{O}{\underset{O}{\diagup}}$$

17                             18 c. A solution of 178 g (0.68 mol) of 18 in 100 mL of CCl$_4$ was stirred and heated at 60°-80° C. while chlorine was passed in as needed and the mixture was irradiated with a sunlamp for 26 hr. Fractionation afforded 243.3 g (90%) of 2,2,3,3-tetrachloro-5,6-bis-(trifluoromethyl)-5,6-difluoro-1,4-dioxane (19), bp 50°-56° C. (9 mm). The 19$_F$ F NMR spectrum and the mass spectrum fit an 86/14 mixture of isomers, presumably trans/cis.

$$\underset{F}{\overset{CF_3}{\underset{CF_3}{\mid}}}\overset{O}{\underset{O}{\diagup}} \xrightarrow{Cl_2, h\nu} \underset{F}{\overset{CF_3}{\underset{CF_3}{\mid}}}\overset{O}{\underset{O}{\diagup}}\overset{Cl_2}{\underset{Cl_2}{}}$$

18                             19 d. A mixture of 240 g (0.60 mol) of 19, 322.2 g (1.8 mol) of SbF$_3$, and 5 mL of SbCl$_5$ was stirred and refluxed for 3 hr. Reaction was continued at 90°-110° C. for 38.5 hrs while six 3-g to 5-g portions of SbCl$_5$ were added intermittently. Volatiles were transferred under vacuum, washed with dil. aq. NaOH solution, dried over CaSO$_4$, filtered and distilled to give 41.2 g (19%) of nearly pure 2,3-dichloro-2,3,5,6-tetrafluoro-5,6-bis(-trifluoromethyl)-1,4-dioxane (20) as a mixture of isomers, bp 58°-62° C. (100 mm) The structure was confirmed by MS and 19$_F$ NMR.

$$\underset{F}{\overset{CF_3}{\underset{CF_3}{\mid}}}\overset{O}{\underset{O}{\diagup}}\overset{Cl_2}{\underset{Cl_2}{}} \xrightarrow{SbF_3/SbCl_5} \underset{F}{\overset{CF_3}{\underset{CF_3}{\mid}}}\overset{O}{\underset{O}{\diagup}}\overset{FCl}{\underset{FCl}{}}$$

19                             20 e. A mixture of 16.4 g (0.25 mol) of zinc dust, 200 mL of dry DMF, and 2 mL of 1,2-dibromoethane was stirred under N₂ while a small portion of 41 g (0.112 mol) of 20 was added. The mixture was heated until reaction had started (ca. 90° C.), then the remainder of 20 was added dropwise at a rate sufficient to maintain temperature up to 105° C. in the pot while product was taken overhead as formed, bp 60°–65° C. When the addition had been completed, the pot temperature was increased until distillate was being collected at 135° C. The distillate was washed with water, dried over CaSO₄, filtered and distilled to afford 14.2 g (43%) of perfluoro-2,3-dimethyl-2,3-dihydro-1,4-dioxin (21), bp 65°–67.5° C.

IR (CCl₄): 1845 (C=C), 1250–1000 cm⁻¹ (CF, C—O). The structure was confirmed as a mixture of the two possible isomers by $^{19}F$ NMR and MS.

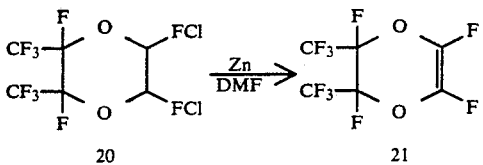

f. A Sealed vial containing 1.7 g (5.8 mmol) of monomer 21 and 5 drops of 2% perfluoropropionyl peroxide catalyst in CFCl₂CF₂Cl was heated at 40° C. for 18 hrs. Addition of 5–25 drops of catalyst solution and heating at 40°–50° C. was repeated ten times. The solution was filtered and evaporated at 25° C. (0.05 mm) to give 0.48 g (28% conv.) of very viscous, clear, colorless homopolymer. The tacky polymer dissolved in CFCl₂CF₂Cl, except for 0.01 g of solid polymer. The volatiles from the polymerization were shown by GC and IR analysis to consist of 1.0 g (59% recov.) of monomer 14 and 0.8 g of CFCl₂CF₂Cl, with very small amounts of other components present.

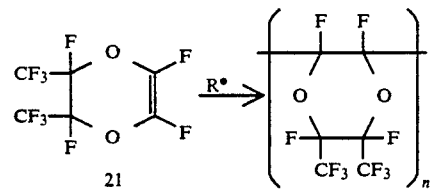

g. An 80 mL metal tube charged with 5.0 g (0.017 mol) of monomer 21, 40 mL of CF₂ClCFCl₂, 3 mL of 2% perfluoropropionyl peroxide catalyst, and 15 g (0.15 mol) of tetrafluoroethylene was shaken at 25° C. for one hr, then at 40° C. for 6 hrs. The solid polymer, 16.3 g after having been dried at 200° C. (0.1 mm), clarified and softened at 295–315° C. on the melting point block. TGA: 4% weight loss at 400° C., 28.5% loss to 540° C. DSC on reheat showed a broad mp, Tonset 280° C., Tpeak 318.5° C. A clear film could be pressed at 330° C. and 2000 psi for 2 min.

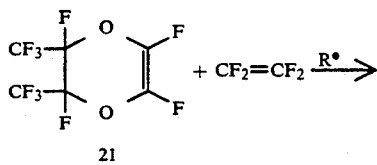

-continued

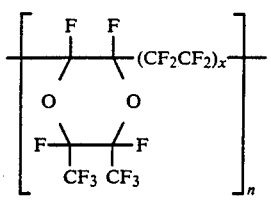

EXAMPLE 5

1,6,7,7,8,8,9,9,-Octafluoro-2,5-dioxabicyclo-[4,3,0]nonane a. A mixture of 148.8 g (2.4 mol) of ethylene glycol and 200 mL of tetrahydrofuran was stirred under N₂ while 23.04 g (0.48 mol) of 50% NaH/mineral oil was added portionwise. When the addition had been completed and gas evolution had ceased, the mixture was stirred at 15°–25° C. while 36.8 g (0.16 mol) of perfluorocyclopentene epoxide was added. After the exothermic reaction had subsided, the mixture was stirred vigorously at 20° C. for one hr and then added to a cold solution of 60 mL of conc. H₂SO₄ in 1200 mL of water. The lower product layer was removed, and the aqueous layer was extracted with 200 mL of ether. The combined organic layers were evaporated at 35° C. (20 mm) to give a viscous residue of crude 22 and tetrahydrofuran.

One mL of DMF was added, and 65 g (0.5 mol) of thionyl chloride was added dropwise. The mixture was heated at 60°–80° C. for 6.5 hrs while gas evolution slowed and nearly ceased. Another 65 g (0.5 mol) of thionyl chloride and 1 mL of DMF were added, and reaction was continued at 82°–85° C. for 5.5 hrs. Fractionation afforded 26.3 g of a cut, bp 63°–65.5° C. (40 mm), composed of 20 g (43%) of intermediate 23 and the remainder by-product Cl(CH₂)₄Cl, identified by GC/MS.

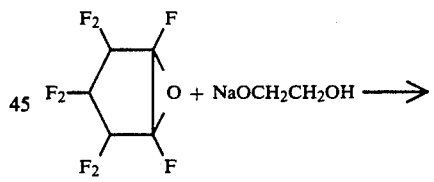

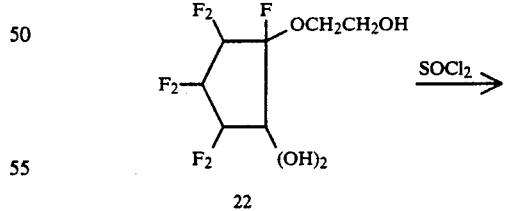

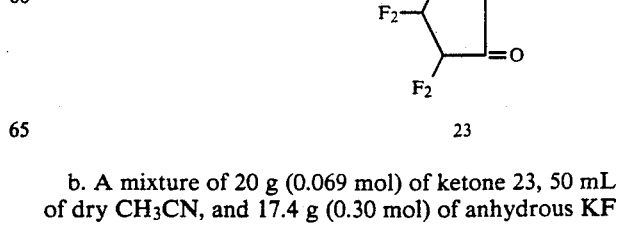

b. A mixture of 20 g (0.069 mol) of ketone 23, 50 mL of dry CH₃CN, and 17.4 g (0.30 mol) of anhydrous KF was stirred and refluxed under N₂ for 17 hrs, then poured into 1 L of water. The lower layer was separated, and the upper layer was extracted with 100 mL of ether. The combined organic layers were dried over CaSO₄, filtered, and distilled to give 10.0 g (53%) of 1,6,7,7,8,8,9,9-octafluoro-2,5-dioxabicyclo[4.3.0]nonane (24), bp 65.5°–68.5° C. (20 mm), identified by NMR and GC/MS.

This intermediate (24) can be converted by the sequence of chlorination, partial exchange of chlorine for fluorine, and dechlorination to the bicyclic monomer 25.

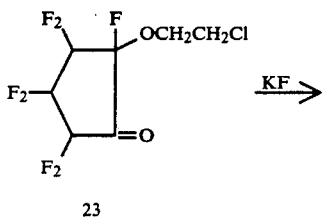

23

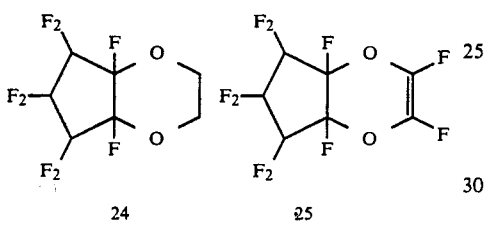

24    25

EXAMPLE 6

Copolymerization of Perfluoro-2-methyl-2,3-dihydro-1,4-dioxin with Ethylene

A 240 mL metal tube charged with 10.0 g (0.042 mol) of 14, 50 mL of CF₂ClCFCl₂, and 0.5 g of Perkadox 16 catalyst was pressured to 1500 psi at 30° C. with ethylene and then agitated at 45° C. until Δp=300 psi (0.03 Pa) (8.5 hr) The moist solid product was stirred with 150 mL more CF₂ClCFCl₂, filtered and rinsed to give 4.9 g of solid copolymer after vacuum drying. Extraction with another 50 mL of CF₂ClCFCl₂ and vacuum drying left 4.5 g of a copolymer which softened and flowed at 95°–110° C. on the melting point block. The polymer was heated at 78° C. (0.03 mm) before analysis.

Anal. Calcd. for C₅F₈O₂·(C₂H₄)₃.₅:
C, 73.48; H, 11.51; F, 12.40;
Found:
C, 72.81; H, 11.10; F, 10.54;
C, 73 03; H, 11.00; F, 10.39;

DSC showed an apparent melting point, Tp 114° C., but no evidence for a glass transition. TGA indicated stability to ca 400° C. and 10% wt-loss at 450° C. A nearly clear, limber film could be pressed at 100° C. and 500 psi for 30 sec.

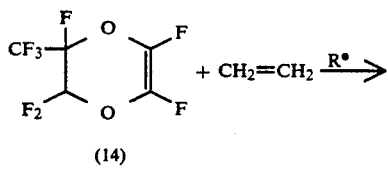

(14)

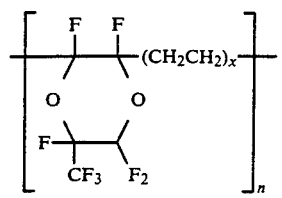

EXAMPLE 7

Copolymerization of Perfluoro-2Methyl 2,3-dihydro-1,4-dioxin with Vinyl Acetate

A 20 mL vial was charged under N₂ with 5.0 g (0.021 mol) of 14, 1.8 g (0.021 mol) of vinyl acetate, and 20 drops of 2% perfluoropropionyl peroxide catalyst in CF₂ClCFCl₂ solution, and the mixture was stirred at 25° C. for 20 hrs. Addition of catalyst was repeated three times over 2 days while viscosity increased and some polymer separated. Removal of volatiles under vacuum gave 84% of recovered 14 and ca 5% of recovered vinyl acetate. The residual polymer (2.2 g) was a tough, somewhat rubbery solid which clarified and flowed at 90°–120° C. on the melting point block. Dissolution of the duct in 40 mL of ethyl acetate and precipitation by addition of 80 mL of hexane afforded 1.9 g of polymer which was dried under vacuum.

Anal. Calcd. for C₅F₈O₂·(C₄H₆O₂)₂₀:
C, 51.93; H, 6.15; F, 7.73;
Found:
C, 52.35; H, 6.70; F, 9.23;
C, 52.43; H, 6.55; F, 9.12;

DSC (2nd heat under N₂) indicated a weak m.p., Tp 2° C., and a Tg 39°–44° C. TGA showed slight loss of volatiles to 110° C (solvent), then no thermal events until onset of decomposition at 323° C., maximum rate occurring at 336° C.

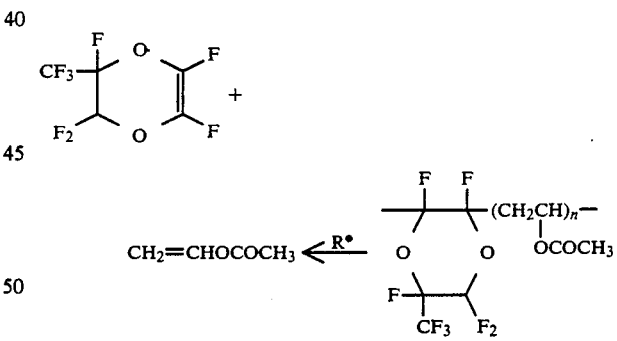

EXAMPLE 8

Preparation of Bis-2,2-trifluoromethyl-4,5-dichloro-1,3-dioxole a. Bromine, 2 ml, was slowly added to a mixture of 40 g zinc dust and 250 ml dimethylformamide. Then 139.2 g bis-2,2-trifluoromethyl-4,4,5,5-tetrachloro-1,3-dioxolane was added slowly while maintaining a temperature of 50°–60° C. The mixture was stirred for one hour and then all the material boiling below 145° C. distilled. The distillate was washed with 200 ml ice water to give 107.5 g of product. Gas chromatographic analysis showed the product to contain 99.6% bis-2,2-trifluoromethyl-4,5-dichloro-1,3-dioxole. Redistillation yielded 4.1 g, 94.0%, bis-2,2-trifluoromethyl-4,5- dichloro-1,3-dioxole, with a boiling point of 89° C. The yield of the reduction product bis-2,2-trifluoromethyl-4-chloro-1,3-dioxole, was 0.25%.

COMPARATIVE EXAMPLE b. A crystal of iodine was added to 19.5 g zinc dust and 220 ml dry 2-(2-ethoxyethoxy)ethanol. Then 90.9 g bis-2,2-trifluoromethyl-4,4,5,5-tetrachlorodioxolane was added slowly while maintaining a temperature of 65°-81° C. The mixture was stirred at ambient temperature for 17 hours and then all the product removed by distillation. The final pot temperature was 190° C. The distillate was washed with 300 ml ice water to give 63.5 g product. Gas chromatographic analysis showed the product to contain 97.2% bis-2,2-trifluoromethyl-4,5-dichloro-1,3-dioxole. Redistillation yielded 60.4 g, 83.5%, bis-2,2-trifluoromethyl-4,5-dichloro-1,3-dioxole, containing 2.3% bis-2,2-tri-fluoromethyl-4-chloro-1,3dioxole as an impurity.

EXAMPLE 9

Preparation of
Bis-2,2-trifluoromethyl-4-chloro-5-fluoro-1,3-dioxole a. A mixture of 42.5 g zinc dust, 150 ml dimethylformamide and 1 ml 1,2-dibromoethane was stirred at ambient temperature for 30 minutes. Then 99.5 g bis-2,2-trifluoromethyl-4,4,5-trichloro-5-fluoro-1,3-dioxolane was added while maintaining a temperature of 45°-55° C. The mixture was stirred for one hour and then distilled until the pot temperature reached 165° C. The 64.3 g distillate was redistilled to give 60.1 g, 77%, bis-2,2-trifluoromethyl-4-chloro-5-fluoro-1,3-dioxole, bp 61° C., which contained 1.0% bis-2,2-trifluoromethyl-4-fluoro-1,3-dioxole, as an impurity.

Comparative Example b. A mixture of 22.9 g zinc dust, 150 ml diethyleneglycol dimethyl ether and 1.0 g iodine was stirred at room temperature for 15 minutes. Then 99.5 g bis-2,2-trifluoromethyl-4,4,5,5-trichloro-5-fluoro-1,3-dioxolane was added. The mixture was heated to 80° C., cooled, stirred at ambient temperature for 16 hours and distilled until the pot temperature reached 160° C. The distillate was washed with 200 ml ice water to give 61.3 product which contained 49% starting material, 37% bis-2,2-trifluoromethyl-4-chloro-5-fluoro-1,3-dioxole, 9% bis-2,2-trifluoromethyl-4-fluoro-1,3-dioxole and 5% cis/trans bis-2,2-trifluoromethyl-4,5-dichloro-4-fluoro-1,3-dioxolane.

EXAMPLE 10

Preparation of
Bis-2,2-trifluoromethyl-4,5-difluoro-1,3-dioxole

A mixture of 15 g zinc dust, 75 ml dimethylformamide and 1 ml bromine was heated to 87° C. and 30.0 g bis-2,2-trifluoromethyl-4,5-dichloro-4,5-difluoro-1,3-dioxolane added. After 10 minutes the temperature of the reaction mixture rose to 106° C. and all the contents distilled until the pot temperature reached 158° C. The distillate, 12.5 g, was a mixture of 11% starting material and 87% bis-2,2-trifluoromethyl-4,5-difluoro-1,3-dioxole. This responds to a 95% conversion of starting dioxolane and a 49% yield of bis-2,2-trifluoromethyl-4,5-difluoro-1,3-dioxole.

As many differing embodiments of this invention may be made without departing from the spirit and scope thereof, it is to be understood that this invention is not limited to the specific embodiments, except as defined in the appended claims.

What is claimed:

1. A fluorodihydrodioxin of the formula

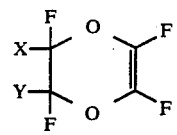

wherein:

X and Y independently are F or $R_F$ provided that X and Y are not both F;

$R_F$ is a $C_1$ to $C_8$ linear or branched ether oxygen; and

X and Y taken together are $(CF_2)n$, where n=2-4.

2. A fluorodihydrodioxin according to claim 1 wherein X is F and Y is $CF_3$.

3. A fluorodihydrodioxin according to claim 1 wherein Y=F and X=$CF_2CF_3$.

4. A fluorodihydrodioxin according to claim 1 wherein Y=F and X=a $C_1$ to $C_8$ linear perfluoroalkyl.

5. A polymer of a dihydrodioxine according to claim 1 produced by free radical polymerization.

6. A copolymer of a dihydrodioxin according to claim 1 with ethylene and/or a fluoroethylene and/or vinyl acetate, containing at least 1% of the dihydrodioxin.

7. A copolymer of a dihydrodioxin according to claim 1 with tetrafluoroethylene, containing at least 1% of the dihydrodioxin.

8. A copolymer of perfluoro-2,3-dihydro-1-4-dioxin with ethylene and/or a fluoroethylene, containing at least 1% of the perfluoro-2,3-dihydro-1-4-dioxin.

9. A coating solution comprising a polymer according to claim 6.

10. A coating solution containing a polymer according to claim 7.

11. A coating solution containing a polymer according to claim 8.

12. A film prepared from the solution according to claim 9.

13. A film prepared from the solution according to claim 10.

14. A film prepared from the solution according to claim 11.

15. A homopolymer of a fluorodihydrodioxin composed of units the formula

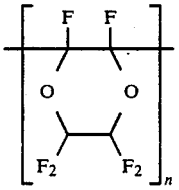

where n=5 or more.

16. A copolymer of

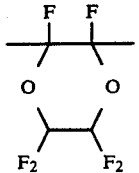

with ethylene and/or a fluoroethylene and/or vinyl acetate.

17. The copolymer of claim 16 containing at least 1% of the dihydrodioxin.

18. A coating solution containing the homopolymer of claim 15.

19. A coating solution containing the copolymer of claim 16.

20. The polymer of claim 5 where X is F, Y is $R_F$ and $R_F$ is $CF_3$.

21. A coating solution containing a polymer according to claim 20.

22. A film prepared from the coating solution of claim 21.

23. A polymer of a dihydrodioxin defined according to claim 1 of the structure

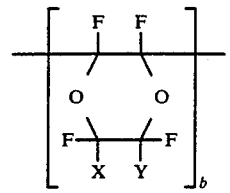

where X and Y are as defined in claim 1 and b is 5 or more.

* * * * *

UNITED STATES PATENT AND TRADEMARK OFFICE
CERTIFICATE OF CORRECTION

PATENT NO. : 5,026,801
DATED : June 25, 1991
INVENTOR(S) : Krespan et al.

It is certified that error appears in the above-identified patent and that said Letters Patent is hereby corrected as shown below:

In the Claims, in Column 22, line 17,

"$R_F$ is a $C_1$ to $C_8$ linear or branched ether oxygen; and"

should read:

--$R_F$ is a $C_1$ to $C_8$ linear or branched perfluoroalkyl, with or without in-chain ether oxygen; and--

Signed and Sealed this

Thirty-first Day of March, 1998

*Attest:*

BRUCE LEHMAN

*Attesting Officer*     *Commissioner of Patents and Trademarks*